US011617725B2

(12) United States Patent
Johnson

(10) Patent No.: US 11,617,725 B2
(45) Date of Patent: *Apr. 4, 2023

(54) COMPOSITIONS INCLUDING A CANNABINOID AND PROTOCATECHUIC ACID

(71) Applicant: Lanny Leo Johnson, Frankfort, MI (US)

(72) Inventor: Lanny Leo Johnson, Frankfort, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/659,907

(22) Filed: Apr. 20, 2022

(65) Prior Publication Data

US 2022/0323374 A1 Oct. 13, 2022

Related U.S. Application Data

(63) Continuation of application No. 17/225,584, filed on Apr. 8, 2021, now Pat. No. 11,337,934.

(51) Int. Cl.
*A61K 31/05* (2006.01)
*A61K 31/192* (2006.01)
*A61K 31/352* (2006.01)

(52) U.S. Cl.
CPC ............ *A61K 31/05* (2013.01); *A61K 31/192* (2013.01); *A61K 31/352* (2013.01)

(58) Field of Classification Search
CPC ..... A61K 31/05; A61K 31/192; A61K 31/352
USPC ....................................................... 514/456
See application file for complete search history.

(56) References Cited

U.S. PATENT DOCUMENTS

| | | | |
|---|---|---|---|
| 8,906,429 B1 | 12/2014 | Kolsky | |
| 9,017,737 B2 | 4/2015 | Kikuchi et al. | |
| 9,066,920 B2 | 6/2015 | Whalley et al. | |
| 9,981,886 B2 | 5/2018 | Ghalili et al. | |
| 10,213,391 B2 | 2/2019 | Singh | |
| 10,617,733 B2 | 4/2020 | Kelly | |
| 11,337,934 B1 * | 5/2022 | Johnson | A61K 31/05 |
| 2020/0000960 A1 | 1/2020 | Kellar et al. | |

FOREIGN PATENT DOCUMENTS

JP          2016003191 A      1/2016

OTHER PUBLICATIONS

Nagarkatti et al , Cannabinoids as novel anti-inflammatory drugs, Future Med Chem. Oct. 2009 ; 1(7): 1333-1349. (Year: 2009).*
Abida Kalsoom Khan et al., Pharmacological Activities of Protocatechuic Acid Acta Poloniae Pharmaceutica—Drug Research, vol. 72 No. 4 pp. 643-650, 2015.
Antonella Casiraghi, Topical Administration of Cannabidiol: Influence of Vehicle-Related Aspects on Skin Permeation Process. Pharmaceuticals 2020, 13, 337, doi:10.3390/ph13110337.
Della Rocca G and Di Salvo A (2020), Hemp in Veterinary Medicine: From Feed to Drug. Front. Vet. Sci. 7:387. doi: 10.3389/fvets.2020.00387.
Dikmen et al., "Cannabinoid system involves in analgesic effect of protocatechuic acid", DARU J Pharm Sci (2019) 27:605-612.
Duygu Yesim Dikmen, Abstract: Cannabinoid system involves in the analgesic effect of protocatechuic acid. SpringerLink. Research article Published: Jul. 19, 2019. DARU Journal of Pharmaceutical Sciences 27, 605-612 (2019).
Fatema Yeasmin and Hyong Woo Choi, Natural Salicylates and Their Roles in Human Health. Int. J. Mol. Sci. 2020, 21, 9049. doi:10.3390/ijms21239049.
HANUS/HOD, Terpenes/Terpenoids in Cannabis: Are They Important? Med Cannabis Cannabinoids 2020;3:25-60 DOI: 10.1159/000509733.
Indication Bioscience, Indication Bioscience Granted First Patent for Statin Plus Cannabidiol (CBD) Combination. Feb. 1, 2021 12:16 UTC. BioSpace.
J. Song, et al, New progress in the pharmacology of protocatechuic acid: A compound ingested in daily foods and herbs frequently and heavily. Elsevier, doi.org/10.1016/j.phrs.2020.105109. Pharmacological Research 161 (2020) 105109.
Jennifer Lutz (/AUTHOR/59048/LURZ), CBD as a Treatment Option for Osteoarthritis? Last updated on Sep. 6, 2020.
Kaemer et al., Decarbonylation: A metabolic pathway of cannabidiol in humans. Wiley Jan. 24, 2019 doi: 10.1002./dta.2572.
Masella et al., Protocatechuic Acid and Human Disease Prevention: Biological Activities and Molecular Mechanisms.ResearchGate. Current Medicinal Chemistry Apr. 2012. DOI: 10.2174/092986712800672102 Source: PubMed.
Miguel Olivas-Aguirre, Phenolic Compounds Cannabidiol, Curcumin and Quercetin Cause Mitochondrial Dysfunction and Suppress Acute Lymphoblastic Leukemia Cells. Int. J. Mol. Sci. 2021, 22, 204. dx.doi.org/10.3390/jms22010204.
Monika Styrzewska, Flax Fiber Hydrophobic Extract Inhibits Human Skin Cells Inflammation and Causes Remodeling of Extracellular Matrix and Wound Closure Activation. Hindawi Publishing Corporation, BioMed Research International, vol. 2015, Article ID 862391, 15 pages http://dx.doi.org/10.1155/2015/862391.
Natascia Bruni, Cannabinoid Delivery Systems for Pain and Inflammation Treatment. Molecules 2018, 23, 2478. doi:10.3390/molecules23102478.
Omid Jalali, Protocatechuic Acid as a Topical Antimicrobial for Surgical Skin Antisepsis.JBJS Open Access d 2020: e19.00079. http: //dx.doi.org/10.2106/JBJS.OA.19.00079.

(Continued)

*Primary Examiner* — Taylor V Oh
(74) *Attorney, Agent, or Firm* — Stonebridge IP, PLLC

(57) ABSTRACT

A composition comprising a therapeutically effective amount of a cannabinoid and protocatechuic acid is provided. The disclosure further provides a method of treating inflammation comprising administering a composition comprising a therapeutically effective amount of a cannabinoid and protocatechuic acid to a patient in need thereof. The disclosure further provides a method of treating inflammation including administering a composition including protocatechuic acid and a composition including a cannabinoid to a patient in need thereof. In embodiments, the composition including protocatechuic acid and the composition including a cannabinoid may be administered simultaneously within about 60 minutes of each other. In embodiments, the cannabinoid includes Cannabidiol (CBD).

10 Claims, No Drawings

(56) References Cited

OTHER PUBLICATIONS

Omid Jalali, Reduced Bacterial Burden of the Skin Surrounding the Shoulder Joint Following Topical Protocatechuic Acid Application. JBJS Open Access d 2020:e19.00078. http: //dx.doi.org/10.2106/JBJS.OA.19.00078.

Project CBD, How CBD Works. 16 pages.

Rosivaldo S. Borges, Understanding the Molecular Aspects of Tetrahydrocannabinol and Cannabidiol as Antioxidants. Molecules 2013, 18, 12663-12674; doi:10.3390/molecules181012663.

Sahil Kakkar and Souravh Bais, A Review on Protocatechuic Acid and Its Pharmacological Potential. Hindawi Publishing Corporation. ISRN Pharmacology. vol. 2014, Article ID 952943, 9 pages, http: //dx.doi.org/10.1155/2014/952943.

Takeda et al., Cannabidiol-2',6'-Dimethyl Ether, a Cannabidiol Derivative, Is a Highly Potent and Selective 15-Lipoxygenase Inhibitor. Aspet Journals, Jun. 23, 2017. doi:10.1124/dmd.109.026930.

W. Chen et al., Pharmacokinetics of protocatechuic acid in mouse and its quantification in human plasma using LC-tandem mass spectrometry. Elsevier B.V. http://dx.doi.org/10.1016/j.jchromb.2012.09.032. B 908 (2012) 39-44.

Wikipedia, Cannabidiol. Last edited on Mar. 15, 2021, at 14:19 (UTC).

Wikipedia, Cannabinoid. Last edited on Mar. 16, 2021, at 21:01 (UTC).

Wikipedia, Medication. Last edited on Mar. 20, 2021, at 13:31 (UTC).

Yoswaris Semaming, Pharmacological Properties of Protocatechuic Acid and Its Potential Roles as Complementary Medicine.Hindawi Publishing Corporation. Evidence-Based Complementary and Alternative Medicine. vol. 2015, Article ID 593902, 11 pages, http: //dx.doi.org/10.1155/2015/593902.

PCT International Search Report, international appl. No. PCT/US2022/023451, dated Jun. 3, 2022.

PCT Written Opinion of the International Searching Authority, international appl. No. PCT/US2022/023451, dated Jun. 3, 2022.

* cited by examiner

COMPOSITIONS INCLUDING A CANNABINOID AND PROTOCATECHUIC ACID

CROSS REFERENCE TO RELATED APPLICATIONS

This application is a continuation of U.S. application Ser. No. 17/225,584, filed on Apr. 8, 2021, which is herein incorporated by reference in its entirety.

BACKGROUND OF THE DISCLOSURE

Field of the Invention

This disclosure is generally directed to compositions including a cannabinoid and protocatechuic acid and methods of treatment using the compositions. In preferred embodiments, the methods of treatment may include treating inflammation. In preferred embodiments, the cannabinoid may include Cannabidiol (CBD).

Description of the Related Art

Cannabinoids are a class of compounds found in cannabis. Phytocannabinoid tetrahydrocannabinol (THC) is a cannabinoid and is regarded as a primary psychoactive compound in cannabis. Cannabidiol (CBD) is another major cannabinoid. There are known to be at least 144 different cannabinoids.

Synthetic cannabinoids are also known. They encompass a variety of chemical groups including those structurally related to THC, as well as cannabimimetics including aminoalkylindoles, 1,5-diarylpyrazoles, quinolines, and arylsulfonamides, as well as eicosanoids which are related to endocannabinoids. Cannabidiol (CBD) is a phytocannabinoid. It can account for up to 40% of a cannabis plant's extract.

Cannabidiol (CBD) as a therapeutic can be administered to a mammal in a variety of ways, including inhalation, by oral delivery, transdermal, as well as through an aerosol. It may be supplied as CBD oil, or hemp oil (extract), or in capsules, dried cannabis, and is also available as a prescription liquid solution. CBD is not known to have the same psycho-activity as THC. In the United States, the cannabidiol drug Epidiolex™ was approved by the Food and Drug Administration for the treatment of epilepsy disorders. The effects of CBD on receptors in the immune system may help reduce overall inflammation in the body. CBD oil may offer benefits for acne management. CBD oil may prevent activity in sebaceous glands. CBD may also prevent cancer cell growth. CBD may also have benefit for neurogenerative disorders.

Protocatechuic acid (PCA) is a dihydroxybenzoic acid. Protocatechuic acid (PCA) is known as an antioxidant and anti-inflammatory. PCA has been variously reported in the literature as having a variety of health benefits.

SUMMARY OF THE INVENTION

A composition comprising a therapeutically effective amount of a cannabinoid and protocatechuic acid is provided. The disclosure further provides a method of treating inflammation comprising administering a composition comprising a therapeutically effective amount of a cannabinoid and protocatechuic acid to a patient in need thereof. The disclosure further provides a method of treating inflammation including administering a composition including protocatechuic acid and a composition including a cannabinoid to a patient in need thereof. In embodiments, the composition including protocatechuic acid and the composition including a cannabinoid may be administered simultaneously within about 60 minutes of each other. In embodiments, the cannabinoid includes cannabidiol (CBD).

The cannabinoid may include a cannabigerol-type compound, cannabichromene-type compound, cannabidiol-type compound, tetrahydrocannabinol and cannabinol-type compound, cannabielsoin-type compound, iso-tetrahydrocannabinol-type compound, cannabicyclol-type compound, and/or a cannabicitran-type compound.

The cannabinoid may include tetrahydrocannabinol (THC), tetrahydrocannabinolic acid (THCA), cannabidiol (CBD), cannabidiolic acid (CBDA), cannabinol (CBN), annabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin CBCV, cannabigerovarin (CBGV), cannabigerol monomethyl ether (CBGM), cannabielsoin (CBE), and/or cannabicitran (CBT).

In preferred embodiments, the cannabinoid includes cannabidiol (CBD). In preferred embodiments, the cannabinoid is cannabidiol (CBD).

PCA is a powerful antioxidant and anti-inflammation reagent. Inflammation is fundamental to all disease. CBD can be used as an adjunct to PCA while providing medicinal properties not known to PCA.

The pharmacology of CBD in not completely known. Side effects are minimal as reported, but still under investigation. The pharmacology of PCA is well established and PCA has no known adverse side effects; no allergy, no mutagenic, no toxicity. In embodiments, the combination of PCA and CBD allows the dose of CBD to be low or well within the known range, yet still achieving health benefits.

Other features and aspects will be apparent from the following detailed description and the claims.

DETAILED DESCRIPTION

The following detailed description is provided to assist the reader in gaining a comprehensive understanding of the methods, products, and/or systems, described herein. However, various changes, modifications, and equivalents of the methods, products, and/or systems described herein will be apparent to an ordinary skilled artisan.

This disclosure is directed to compositions including cannabinoids and protocatechuic acid. The cannabinoids may include any of the class of compounds generally recognized as cannabinoids deriving from the cannabis plant. In a preferred embodiment, the cannabinoid may be cannabidiol. The cannabinoids may be a naturally occurring compound or can be prepared synthetically.

Cannabinoids may interact with, or mediate, the cannabinoid receptors CB1 and/or CB2. The cannabinoids may also interact with the 'endocannabinoid system' which consists of cannabinoid receptors, as well as ligands of cannabinoid receptors (endocannabinoids) and various enzymes. The endocannabinoid system is involved in many important physiological functions in the central and peripheral nervous systems and in the endocrine and immune systems of a mammal.

Cannabinoids may be extracted from a plant with organic solvents. Hydrocarbons and alcohols may be used. Supercritical solvent extraction with carbon dioxide may also be used. Once extracted, isolated components can be separated using distillation or other standard separation techniques. As mentioned above, cannabinoids of the disclosure may also be synthetically prepared. A standard CBD crystal is about 4.44 micrometers (4,440 nanometers). Whereas, Nano CBD is less than 100 nanometers.

The cannabinoids of the disclosure may include the following classes of compounds: Cannabigerol-type, Cannabichromene-type, Cannabidiol-type, Tetrahydrocannabinol and Cannabinol-type, Cannabielsoin-type, iso-Tetrahydrocannabinol-type, Cannabicyclol-type, and Cannabicitran-type.

Cannabinoids of the disclosure include: Tetrahydrocannabinol (THC), tetrahydrocannabinolic acid (THCA), Cannabidiol (CBD), cannabidiolic acid (CBDA), Cannabinol (CBN), Cannabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin CBCV, cannabigerovarin (CBGV), cannabigerol monomethyl ether (CBGM), cannabielsoin (CBE), cannabicitran (CBT).

Cannabinoids of the disclosure may have anti-inflammatory, antioxidative, antiemetic, antipsychotic, and/or neuroprotective properties. Cannabinoids of the disclosure may be able to treat anxiety, addiction, appetite, sleep disorders, pain perception, nausea, and vomiting. Cannabinoids of the disclosure may treat osteoarthritis. Cannabinoids of the disclosure may be useful for pain management. Cannabinoids of the disclosure may be useful for the treatment of cancer.

Compositions of the disclosure may treat redox balance by modifying the level and activity of both oxidants and antioxidants. Compositions of the disclosure may interrupt free radical chain reactions, capturing free radicals or transforming them into less reactive forms.

The treatments may encompass inflammatory, nociceptive, and neuropathic pain. CBD is an exogenous (out of the body) cannabinoid that acts on the endogenous (in the body) cannabinoid system to function in an antioxidant capacity, decrease inflammation and act as an analgesic.

Treatment with compositions of the disclosure may slow the progression of osteoarthritis by decreasing inflammation, both systematically and locally. The interaction of compositions of the invention with the immune system and its potential antioxidant affect helps to decrease symptoms associated with osteoarthritis and improve quality of life.

Administering compositions of the invention can block pain signals from reaching the brain by binding to specific pain receptors. Administering compositions of the invention may attenuate central sensation and neuropathic pain development. Administering compositions of the invention may decrease pain sensations locally by reducing mechanosensitivity of joint nociceptors. Administering compositions of the invention may reduce joint swelling and decrease immune cell infiltration, inflammation, and thickening of the connective tissue that lines joints. Administering compositions of the invention may reduce acute, inflammatory changes. Administering compositions of the invention may reduce production of inflammatory cytokines. Administering compositions of the invention may relieve anxiety and sleep disturbances associated with chronic pain conditions.

The mechanism of action may differ between PCA and CBD. PCA may work by an anabolic stimulation by increasing the genetic expression of the growth hormone IGF-1 and other anabolic cytokines; IL-4 and IL-10. At the same time, inflammatory catabolic cytokines are reduced. CBD may act as a serotonin receptor partial agonist. It is an allosteric modulator of the μ and δ-opioid receptors as well. The pharmacological effects of CBD may involve PPARγ agonism, inhibition of voltage-gated cation channels, and intracellular calcium release.

Protocatechuic acid (PCA) is a phytochemical, a powerful antioxidant, which is found in nature. There are no known human toxic effects of PCA. PCA is non-allergenic and a non-inflammatory. It is also non-mutagenic. Importantly for a new therapeutic, protocatechuic acid (PCA) has been designated as Generally Recognized As Safe (GRAS) by the FDA as a food flavoring substance. PCA may be biochemically manufactured and/or extracted from plants in an amorphous or crystalline state. Both states have anti-viral properties of low pH, anti-protease, docking blocker and hormonal and cellular immunity remains inherent in the molecule.

As mentioned, protocatechuic acid (PCA) is a compound with powerful anti-inflammatory properties. One of the ways the human body responds to PCA is with a massive anti-inflammatory response. The pathological effect seen in clinical cases of SARS Co-2 has been termed a 'cytokine storm' in the lungs. PCA is a powerful anti-inflammatory by its anti-catabolic cytokine blocker properties. PCA acts as a tyrosinase inhibitor in other applications. PCA is also a protease inhibitor. PCA has anti-viral docking properties.

Protocatechuic acid (PCA) is thus a broad-spectrum antiviral destroying antibiotic when coating of cloth and/or metal surfaces. PCA crystals have the physical properties of a crystal with sharp protrusions that may disrupt the coating of microbes in the dry state or in solution. Protocatechuic acid (PCA) has a viricidal effect on the SARS CoV2 virus. SARS CoV-2 virus retains its viability and pathogenesis in aqueous medium; in animals, humans and in air borne droplets.

The compositions of the invention can be administered in a variety of ways, including, by oral delivery, inhalation, intravenous, topical, and transdermal, an aerosol including an oromucosal spray, pulmonary administration, as well as nanotechnology-based approaches. The therapeutic compositions and compounds may be administered, for example, by buccal, injection, pulmonary, inhalant, subcutaneous, and sublingual delivery.

The present invention also provides compositions that may be administered to localized affected areas of a mammal as well. This would include the skin, lungs, and nasal cavities. The present disclosure also provides compositions and methods for use in the treatment of symptoms related to Covid-19.

In embodiments the administration may be by intraperitoneal routes. Also disclosed is a method of treating a pathological condition comprising the coating of skin, oral cavity, nares, nasopharynx, and pulmonary tree with compositions of the invention.

In embodiments, the present disclosure provides multiple routes of therapeutic delivery. Normal size crystals (e.g., approximately 177 μm or micrometer or 40 times larger than CBD) and powder may be delivered by an oral route. Smaller sized crystals and particles may also be used for intravenous, intraperitoneal and aerosol delivery to a patient. By comparison a red blood cell is approximately 7.5 to 8.7 μm in diameter and 1.7 to 2.2 μm in thickness.

Further by way of example, the pharmaceutical composition can comprise a pharmaceutically acceptable carrier. By way of example, the pharmaceutically acceptable carrier can be selected from, but not limited to, any carrier, diluent, or excipient compatible with the other ingredients of the composition.

Further by way of example, the pharmaceutical composition can comprise an acceptable delivery carrier. By way of example, the delivery can be formulated and administered as known in the art, e.g., for topical, oral, buccal, including lozenges, injection, intravenous, inhalant, subcutaneous, sublingual and/or transdermal. Further, said topical delivery carrier may be formulated and administered to any surface or cavity of the body.

By way of example, the acceptable delivery can be selected from any dermal or transdermal carrier compatible with the other ingredients of the composition. In some embodiments, the acceptable delivery carrier is a biodegradable microsphere or a slow release bioabsorbable material. By way of example, the acceptable delivery carrier can be selected from 50/50 D, L lactide/glycolide or 85/15 D, L lactide/glycolide, both of which are amorphous physically and, therefore, are non-reactive when used as a carrier in a composition that is delivered in or to the body.

In embodiments, the pharmaceutical composition may be formulated for an aerosol spray. The aerosol spray may include a liquid vehicle and a stabilizer. The liquid vehicle may include water, or an alcohol and the stabilizer may include an oil. In preferred embodiments, the oil is an essential oil. In preferred embodiments, the essential oil may be lemon oil. In embodiments, the aerosol spray compositions may comprise principally the active ingredients, liquid vehicle, and stabilizer as the main ingredients.

In embodiments, the administration of the cannabinoid and the protocatechuic acid may be by the same route. In embodiments, the administration of the cannabinoid and protocatechuic acid may be by different routes and may be simultaneous or essentially simultaneous.

Simultaneous as used herein means that both compositions will be administered such that both compositions (or their metabolites) will be substantially present in the body of the patient at the same time. This may thus encompass administration at the same time or at nearly the same time, for example, within about 60 minutes of each other, or preferably within about 30 minutes, or more preferably within about 15 minutes.

For example, the cannabinoid and the protocatechuic acid may be in a single composition or formulation, e.g., a pill or tablet, or the like. In other embodiments, the cannabinoid and the protocatechuic acid may be administered separately. For example, the protocatechuic acid may be in a pill or tablet and the cannabinoid may be administered transdermally.

A pharmaceutical composition as used herein generally refers to a medication (also referred to as medicine, pharmaceutical drug, medicinal drug or simply drug) and that is used to diagnose, cure, treat, or prevent disease. See Medicine, Wikipedia, The Free Encyclopedia, Date of last revision: 21 Mar. 2021, herein incorporated by reference.

The metabolism of cannabinoids and PCA is to enter the body by potentially different routes but both go to the liver and become metabolized. The various metabolites perfuse the body and are eventually eliminated via the kidney (urine) or bowel (feces).

Bio availability of each in the body are different and therefore presents a need for combination to maximize the effect. The oral bioavailability of cannabidiol is approximately 6% in humans while bioavailability by inhalation is 11-45% (mean of 31%).

The oral availability of PCA is 100% in 30 minutes. Therefore, different routes may be complementary depending upon a patient's condition; for instance, in a burn case the topical route would not be available, but inhalation would. When inhalation is not available, then oral could be used for both. In the alternative, the CBD route could be by inhalation and/or skin and PCA by oral delivery. Intravenous and intra peritoneal are also available for PCA.

The duration of each in the body is different. The elimination half-life of CBD is 18-32 hours. PCA has a peak at 2 minutes and life of 8 hours. The duration planning in therapeutic prescriptions is important for peak effects and duration thereof to achieve maximum benefit.

In certain embodiments, the route of administration is oral. Powdered active ingredient can be mixed with a suitable liquid for drinking or gavage or alternatively, the active ingredient can be in the form of a pill or capsule. The active ingredient may also be mixed with other solid eatable ingredients, such as for an example, in a nutrition/snack bar.

For purposes of the present invention, a pharmaceutical composition is preferably formulated in a unit dosage and in an injectable or infusible form such as solution, suspension, or emulsion. It can also be in the form of a lyophilized powder, which can be converted into solution, suspension, or emulsion before administration. In some embodiments a pharmaceutical composition is provided in a formulation that includes biodegradable microspheres or of amorphous bioabsorbable material of glucose itself. The common biodegradable carriers are importantly amorphous physically and as opposed to crystalline material, do not cause tissue irritation.

In some preferred embodiments the composition is administered together with 50/50 D, L. lactide/glycolide or 85/15 D, L lactide glycolide. Also encompassed herein are nanospheres as known in the pharmaceutical arts. The pharmaceutical compositions may be sterilized by membrane filtration, autoclaving, irradiation and the like and may be stored in unit-dose or multi-dose containers such as sealed vials or ampules. As a non-limiting example, a dose pack may contain 3-5 vials for administration. The first injected initially at the office or at surgery then the remaining vials to be administered over time, such as periodically over weeks. In some instances, glucose may form a portion of the delivery vehicle, whereupon release it enhances the chondroreparative features of the composition.

Methods of formulating pharmaceutical compositions are generally known in the art and are applicable with the instant invention. For instance, the active ingredients may be mixed together with the pharmaceutically acceptable carrier or salt. Thorough discussions of formulation development and selection of pharmaceutically acceptable carriers, stabilizers, coloring, and flavoring agents and like can be found in a variety of pharmaceutical texts known to those skilled in the art, such as Remington's Pharmaceutical Sciences (Mack Publishing Co., Eaton, Pa.), the contents of which are herein incorporated by reference in its entirety.

In some embodiments, the compositions of the present invention are formulated in a sustained-release formula to prolong the presence of the compounds in the treated subject, generally for longer than one day. Many methods of preparing sustained release formulations are known in the art and are available in a variety of publications, including Remington's Pharmaceutical Sciences, cited and incorporated by reference above. In some instances, the active ingredients and optionally glucose is trapped in semipermeable matrices of solid hydrophobic polymers. The matrices can be shaped into films, coatings, microcapsules, or microspheres and administered as known by those skilled in the appropriate art. Any suitable ratio may be used, which may in part depend on the desired matrix. As a nonlimiting example, the pharmaceutical may be provided with a biodegradable polymer formed from about 85/15 or 50/50 D, L lactide/glycolide. The matrices may be a variety from a variety of materials; solids and meshes.

EXAMPLES

Protocatechuic acid (PCA) and cannabidiol (CBD) are new reagents with health and wellness benefits. There is a need for the combination of these drugs to deliver their shared benefits of being an antioxidant and anti-inflammatory reagents. In addition, each have independent benefits not found in the other, whereby the combination synergistically brings all the benefits of each.

Various vehicles were tested with each and in combination. The below data shows that propylene glycol and an alcohol provide an excellent vehicle for combination. Distilled and deionized water are restricted in amounts independently and when placed in combination. The combination of PCA and CBD can be delivered companionably.

Protocatechuic acid (PCA) and cannabidiol (CBD) can be combined for therapeutic purposes. PCA and CBD have recently emerged as novel health and wellness reagents. They are phytochemicals in the nutraceutical, food supplement category. Antioxidants are fundamental to health. Inflammation is the basis of all disease. Each of these reagents have differing additional pharmaceutical properties that would complement each other for a potential important role in health and wellness.

PCA is generally water soluble, but not oil soluble. CBD is oil based and therefore soluble in oil but has restricted solubility in water. Various means can be used to increase the solubility of CBD in water. Emulsification is one method, but is not necessarily a water-soluble product, only water compatible. Another method produces an isolate of CBD. The isolate is a fine powder produced by glycosylation or the attachment of a sugar molecule. The isolate is closer to water soluble.

There is a need in this context to select a pharmacological liquid vehicle that will provide an optimal dose of when combined. Various evidence would condition the manufacturing of the combinations; preliminary low-level warming of the vehicle, while avoiding temperatures above 100 degrees Fahrenheit.

Basic science studies have shown PCA to stimulate human and animal synovium to produce IGF-1 a growth hormone that acts as a disease modifying osteoarthritic drug (DMOAD). There is further evidence that PCA is a broad-spectrum antibiotic, a biofilm destroyer and has antiviral properties including SARS CoV2. Furthermore, its anti-inflammatory properties extend to inflammation of the human skin, including action as an antiseptic for skin pathogens, including C. acnes. PCA in human and animal experiments demonstrate the properties to increase the expression of local growth factors; resulting in wound healing, cartilage repair, and accelerated bone growth. There is additional evidence that PCA has beneficial therapeutic effect upon cellular and hormonal immunity.

CBD is from the hemp plant. It is manufactured with restriction of the psychoactive tetrahydrocannabinol (THC). CDB may have 0-3% THC. THC is the main psychoactive cannabinoid found in cannabis and common to marijuana. CBD is not psychoactive.

CBD has been reported to benefit a wide variety of health issues. CBD is effective in treating some of the cruelest childhood epilepsy syndromes, such as Dravet syndrome and Lennox-Gastaut syndrome (LGS), which typically don't respond to antiseizure medications. In numerous studies, CBD was able to reduce the number of seizures, and in some cases it was able to stop them altogether. Recently the FDA approved the first ever cannabis-derived medicine for these conditions, Epidiolex™, which contains CBD.

CBD is commonly used to address anxiety, and for patients who suffer through the misery of insomnia, studies suggest that CBD may help with both falling asleep and staying asleep.

CBD treats different types of chronic pain. CBD applied on the skin may help lower pain and inflammation due to arthritis. CBD inhibits inflammatory and neuropathic pain, two of the most difficult types of chronic pain to treat.

Solubility

PCA: The solubility of PCA is known in water (1.24%), isopropyl alcohol (30%), denatured ethanol (30%), and propylene glycol (15%). It is not known in deionized water. It is generally not soluble in oil.

CBD: CBD is soluble in oil by nature of the oil-based hemp product. Solvents such as ethanol, methanol, DMSO, and dimethyl formamide purged with an inert gas can be used. The solubility of cannabidiol in these solvents is approximately 35, 30, 60, and 50 mg/ml, respectively.

Materials: The materials were 99% pure PCA and a proprietary 98% pure water-soluble CBD isolate with zero percent HTC. The liquid vehicles used are considered G.R.A.S. by FDA; distilled water, deionized water, propylene glycol and 70% isopropyl alcohol. The test containers were 125-milliliter graduated and measured sterile plastic from Wheaton company. A thermometer probe was used to assess the temperatures.

Method: The first experiment was to identify the PCA and CBD crystals by microscopically, including polarized light. Each crystal was visualized in dry state, followed by soaking crystals on a histology glass slide in distilled water, deionized water, propylene glycol, and isopropyl alcohol. This provided a base line for physical shapes of each of the regents; CBD and PCA for future identification when both are in solution.

The physical properties of each were easily identifiable by polarized light microscopy. It was learned they have distinct physical properties under polarized light microscopy for identification.

PCA has a sharp spear like physical shape. CBD has clusters of thick rod-shaped crystals often on top of each other. Both showed varying amounts of color when refracted by polarized light.

An additional method was employed to replicate the clinical topical application. A smear of the various concentrations was made on the glass histology blank slide to show the amount of crystals deployed for the various concentrations.

CBD crystals were observed in deionized water. PCA crystals were observed in propylene glycol. 10× Polarized light microscopy inspection clearly shows the different physical shapes of each.

Testing was done to determine the independent solubility of each reagent in the various vehicles. This was followed by testing the potential concentrations of each when combined. The testing started with an arbitrary solution concentration, one that could be altered for percentage of solubility.

CBD Solubility Testing

Oil: CBD isolate is naturally oil soluble. It will fully dissolve the white powder into any oil. Warming and or stirring or shaking may be required to move the isolate into solution. It usually takes about 10-15 minutes to fully dissolve. Combined testing in oil was not performed as PCA is not soluble in oil.

Distilled Water: Distilled water is a possible vehicle. CBD was tested at 1.0 gram (1%) in 100 milliliters of distilled water. CBD did not readily dissolve in 100 ml of distilled water at room temperature of 69 degrees Fahrenheit. Heating to 120 degrees Fahrenheit was necessary for dissolving. Upon cooling the CBD went out of solution. There was CBD on the wall of the plastic container throughout; at the sides and bottom with a glue-like tan material. There was a ring around the inside of the container at the level of the water. There was CBD spattered coating of the container wall above the fluid line. There was a reaction during the heating that produced a gas that caused the sealed plastic container to expand. Loosening of the cap gave relief to the expanded plastic container to return to original configuration.

1 gram of CBD in 50 ml distilled water after cooling showed the reagent totally coating the inside of the container; a tan glue-like material on bottom and the sides. There was bead like coating above the water line, delivered by the gaseous state.

The next test was performed in a similar manner with a reduced amount of water-soluble CBD isolate to 0.247 milligrams (0.247%). It did not readily dissolve in 100 ml of distilled water at room temperature of 69 degrees Fahrenheit. Heating to 120 degrees Fahrenheit was necessary for dissolving. Heating prior to adding the CBD proved to be a more effective method to hasten the solubility. Upon cooling the CBD went out of solution. There was CBD on a wall of the plastic container throughout; at the sides and bottom with a glue-like tan material. There was a ring around the inside of the container at the level of the water. There was CBD spattered coating of the container wall above the fluid line. This was anticipated during the procedure as there was a reaction causing the sealed container to expand as though gas was produced. Loosening of the cap gave relief to the expanded plastic container to return to original configuration.

A reduction to 0.247 gram CBD in distilled water produced the same result.

A further reduction in concentration was used in the next experiment; 40 milligrams of CBD in distilled water. 40 mg is the recommended daily oral dose of CBD. Heating to 105 Fahrenheit did not dissolve. It required 140 degrees Fahrenheit to dissolve. No gaseous expansion occurred as with larger concentrations. This is only a 0.04% CBD. For reference, PCA is 1.24% soluble in distilled water.

Deionized water: 1.025 grams of CBD was placed in 50 milliliters of deionized water at room temperature water. It only went into solution at 120 Fahrenheit. After cooling all the CBD came out of solution with similar appearance as distilled water. The failure was as 2.05 grams per 100 ml or a 2.05% solution.

1.025 grams CBD isolate in 50 ml. deionized water shows failure of going into solution.

Therefore, a similar test was performed with a lesser amount of CBD; 0.517 milligrams of water-soluble CBD in 50 milliliters of deionized water. Preliminary heating of the water facilitated the CBD into solution. Upon cooling and 24 hours later, the CBD was still in solution. The percentage of CBD isolate in solution was 1.34% CBD in deionized water. This is similar to distilled water. It also is similar in percentage to PCA which is 1.24% in water. 0.5 grams CBD in deionized water remained in solution for at least 48 hours in this test.

Propylene glycol: Initial testing with propylene glycol was at 2 grams (4%) in 50 milliliters of propylene glycol. This did not go into solution even with heating. The expansion of the plastic capped bottle happened indicating gas production. Removal of lid resulted in expression of gas and return of the bottle to original shape. Then propylene glycol was added to the 100-milliliter level. The procedure was repeated and then 2% CBD went into solution with the same gaseous expansion and release. Upon cooling the CBD came out of solution.

2 grams of CBD in 50 ml. propylene glycol was not dissolved even on heating.

The test was repeated with lesser amount of CBD; 1-gram (1%) CBD in 100 milliliters of propylene glycol. This went easily into solution with preliminary heating to 120 Fahrenheit. CBD remained in solution past 48 hours after cooling.

1 gram of CBD in 100 ml of propylene glycol remained in solution beyond 48 hours.

Alcohol: Ethanol and or isopropyl alcohol is used for industrial extraction of CBD from the hemp fiber. Therefore, it has a very high solubility in alcohol. Initial testing was performed at 1% concentration.

1.02 gram of CBD in 100 ml of isopropyl alcohol was soluble more than 48 hours. It also was performed with 3 grams CBD in 97 ml of 70% isopropyl alcohol.

3 grams of CBD in 100 ml of 70% isopropyl alcohol remained soluble more than 48 hours.

Results: The dry raw material of PCA and water-soluble CBD isolate may be combined in any ratio for potential prescription purposes. However, the route and/or vehicle may present restrictions or limitations on various combinations in the following liquid vehicles.

Distilled water: CBD was soluble at only 0.04%. PCA is 1.24% soluble in distilled water.

Deionized water: CBD (1.34%) and PCA (1.24%) are similar in solubility in deionized water.

Propylene glycol: CBD is soluble at 1% while PCA is soluble up to 15% in propylene glycol.

Isopropyl alcohol: 1.024 mg (1%) to 3 grams of CBD isolate in 70% isopropyl alcohol was readily absorbed at room temperature (68 degrees Fahrenheit) and/or with mobilization of the crystals with minimal shaking. No heating was required.

Testing of Smear on Glass Slide: This clearly demonstrated that 1% concentrations of CBD showed very sparse crystals. The concentrations of 2 and 3% showed abundant crystals of both CBD and PCA.

Heating caused a gaseous reaction that expanded the capped container.

Subsequent Testing on Combinations: Based upon the above individual findings further testing was done on the combinations of the two reagents to seek maximum concentrations in combination for clinical applications.

Propylene Glycol: The first test was the combination of equal proportions of 0.5 grams of CBD and PCA in propylene glycol. Propylene glycol is a commonly used FDA G.R.A.S. reagent in the food industry in a wide variety of consumer products.

1: An attempt to replicate the solubility of 1 gram, 0.497 mg CBD and 0.501 mg of PCA put on top of 99 ml of propylene glycol in a sterile plastic container. The CBD floated on top. When the PCA was added both reagents went to the bottom without dissolving. The reagents went into solution quickly after a few moments of shaking. Importantly heating was not necessary.

0.50 grams CBD and 0.49 grams of PCA in 100 ml propylene glycol dissolved in solution for more than 48 hours.

2: Then tested CBD at increased amounts; its known maximum of 1% (1.04 gm) in propylene glycol with PCA at 1% (0.97 gram). The PCA first floated and fell to bottom. The CBD went to bottom and in tan globule. Shaking mobilized into suspension and gradually settled to the bottom. Heated for 30 seconds to 140° F. Minimal shaking caused all few particles to go into solution. There was no gaseous expansion observed. The combination of 1 gram each of CBD and PCA remained in solution more than 48 hours.

Deionized water: The next test was the combination of equal proportions of 1.0 grams of CBD and PCA in deionized water. Deionized water is a commonly used FDA G.R.A.S. reagent for topical applications and some oral prescriptions.

0.993 grams of CBD added to 20 seconds heated 98 milliliters deionized water (100 degrees Fahrenheit). Then 1.1 PCA added. Shaking left powder at water level in jar. Temperature to 95° F. and not dissolved. Temp to 120° F. and not dissolved as floating on top of water. So, heated further to 140 Fahrenheit. The tan "glue" adhered to the sides and at the water level.

This amount of CBD and PCA did not go into solution. A tan glue-like material was often seen following heating of CBD in solution.

Note: It appears that CBD solute when heated past 100 Fahrenheit forms a tan "glue" like material.

The amounts were reduced to PCA 0.493 and CBD to 0.506 grams. The PCA into room temperature deionized water went to bottom and partially mixed. The CBD floated on top of water. Shaking would not mix. Heating to 100 degrees F. and 120 degrees F. did not mix the CBD and tan glue on the sides. This lesser amount of PCA and CBD did not go into solution, plus there was the tan glue of CBD on the sides of the container.

The amounts were further reduced to PCA 0.26 and CBD to 0.243 grams. The PCA into room temperature deionized water went to bottom and partially mixed. The CBD floated on top of water. Shaking would not mix. Heating to 100 degrees F. and 120 degrees F. did not mix the CBD and tan glue on the sides. Even this lesser amount of PCA and CBD did not go into solution, plus there was the tan glue of CBD on the sides.

Further reductions in amounts of the combination in deionized water would likely be below a therapeutic level of PCA, even as only 40 milligrams of CBD is the recommended daily oral dose. A further reduction may be tried for topical application, but then the threshold of CBD would be far below the 1 to 3 gram amounts.

These reagents could be administered separately in deionized water.

Distilled water: The 0.04% of CBD in distilled water is very limiting in concentration so its combination with PCA was deferred to a later time. CBD at 40 mg could be used separately by oral route. The 1.24% of PCA may be used in distilled water independently.

Alcohol: 3 grams of CBD and 3 grams of PCA were placed in 94 milliliters of 70 isopropyl alcohol at room temperature. Most went into solution immediately. Shaking of the vial resulted in the few clumps to go into solution. This combination concentration exceeds dose parameters of each.

3 grams of CBD and 3 grams of PCA in 100 ml isopropyl alcohol remained in solution for more than 48 hours.

Microscopic Inspection of Combinations of CBD and PCA: This alcohol solution was used to identify the two individual crystals within the solutions. A swab of the 3 grams of CBD and 3 grams of PCA in 70% isopropyl alcohol was examined under polarized light. There were abundant crystals of both reagents. Visualization during the drying phase on the histology glass slide showed the sudden expansion of the spike shaped PCA; virtually growing during the drying phase. The clinical significance is the immediate presence of the PCA shapes that disrupt the skin of microbes leading to death. Abundant crystals were easily identified.

The following polarized light photomicrographs were obtained:

Polarized light photomicrograph of PCA and CBD crystals; 4×;

Polarized light photomicrograph of PCA and CBD crystals; 40×;

Polarized light photomicrograph of CBD crystals; 4×;

Polarized light photomicrograph of CBD crystals; 10×;

Polarized light photomicrograph of PCA and CBD crystals; 10×;

Polarized light photomicrograph of CBD crystals; 40×;

Polarized light photomicrograph of PCA crystals 10×;

Polarized light photomicrograph of CBD and PCA crystals 40×.

The above polarized light photomicrographs demonstrated that the independent crystalline physical shapes remain intact in a combination of PCA and CBD delivered in solution.

PCA and the commonly available oil-based CBD dry raw materials may be physically combined at any ratio for therapeutic purposes. The dose and delivery route may be oral, intra venous, or intraperitoneal, and topical pending the clinical condition under consideration.

The combination of dry CBD isolate powder and PCA crystals may be combined physically in any ratio for similar purposes.

The exploration of dry raw material combinations in solution was conditioned by the reported prescribed dose of each depending upon the application. For an oral route, there is no unsafe practical limit for PCA. The usual oral dose of PCA is delivered in a 500 mg capsule, liquid, gummy, or tablet. The amount per day may be up to 2 tablets four times a day, providing under health care supervision. The recommended daily oral dose of CBD is 20-40 milligrams.

The use of a liquid vehicle for PCA and CBD delivery places conditions heretofore unknown on the doses and concentrations and were identified in this study. The nature of the different vehicles places limitations of dose and concentration on PCA and CBD independently and in combination.

The combination solubility testing is only possible with use of a water-soluble CBD isolate since PCA is not easily soluble in oil. The solubility of each of the reagents and their reaction and solubility in combination are now known. The two reagents may differ in solubility alone and or in combination.

PCA is soluble in water, but not readily soluble in an oil vehicle. CBD is naturally oil based and not readily soluble in a water vehicle. PCA crystals and the natural oil-based CBD powder are restricted in liquid vehicle combination since an oil and water vehicle do not mix. Attempts as such would only allow the CBD to be in suspension without solubility. Therefore, any attempts to combine PCA and CBD require the CBD to be a water-soluble CBD powder for any and all potential therapeutic, health and or wellness preparations.

This example used a proprietary water-soluble CBD solute with PCA crystals for potential combination prescription purposes.

The prescription amount for topical application allows a more widely diverse amounts of PCA and CBD. For instance, a topical dose as small as 25 uM PCA is sufficient for controlling a mammalian skin wound of MRSA and Pseudomonas while healing the wound in 2 days. There is no known upper limit for PCA but a typical concentration is up to a 30% concentration in alcohol vehicle. CBD has no reported lower limit for effective topical application, but the slide smear test indicates that 2-3% concentration would be necessary to leave abundant residual of crystals. In arthritis a 3-gram amount is recommended for topical application for treatment of arthritis. This study showed that this amount in 100 milliliters of isopropyl alcohol showed CBD crystals completely covering of the area of application.

The material and the methods of this study were performed with these parameters in mind. The search for the concentration within each vehicle was explored searching for the parameters that would be clinically practical as well as safe and effective.

Propylene glycol and deionized water liquid vehicle had similar independent solubility. However, even at concentrations below prescribed amounts, the combination did not go into solution.

There is a similar potential of similar concentration combinations with alcohol since both PCA and CBD allow 30% or more concentrations. There does not appear to be any practical concentration limitation in the combination in alcohol. In alcohol, based by the literature CBD would be up to 90% plus at the original time of extraction. PCA has up to 30% solubility in 70% isopropyl alcohol and 60% denatured ethanol. 3 grams was easily and rapidly into solution at room temperature (69 degrees Fahrenheit).

The most interesting finding was the limitation of CBD solubility in distilled water at 0.04% while PCA was known to be 1.24% from previous studies. There is no apparent explanation for the low percentage of CBD in distilled water in this proprietary formula. Other water-soluble CBD sources may be different.

Information was gained concerning manufacturing of CBD alone or in combination. Preliminary heating of the liquid vehicle facilitated solubility and therefore would be important in manufacturing. The potential for gas expansion with heating is another important observation to be addressed during manufacturing even as low as 100 degrees Fahrenheit.

This example established the potential ways heretofore unknown of combining PCA and CBD for use in clinical medicine. In this study, the practical optimal amounts of each reagent and vehicle were identified.

In the dry crystal of PCA or powder state of CBD are effectively combined physically in any amounts.

The potential for combination of PCA and CBD in various liquid vehicles showed great variance. In such cases as below, the optimal combination may be best delivered separately in an optimal vehicle. In other vehicles like propylene glycol and iso-propyl alcohol the amounts of crystals in solution were up to 15-30% and well beyond the generally prescribed dose.

A review of each reagent shows widely different solubility concentration when alone or in combination.

Distilled water:
PCA is soluble up to 1.24%.
CBD is soluble up to 0.04%.
The combination was deferred as the low level of CBD concentration would likely be good for oral application which would be preferred.

Deionized water:
PCA is soluble up to 1.24%.
CBD is soluble up to 1.34%.
The combination is not soluble at concentrations below recommended dose.

Propylene glycol:
PCA is soluble up to 15%.
CBD is soluble up to 1%.
The combination was good at concentration level beyond the generally recommended dose.

Isopropyl alcohol:
PCA is soluble up to 30% concentration.
CBD is soluble up to 90%+ concentration.
The combination was effective at 3% of each, well beyond any anticipated dose.

Each of the % concentrations in these examples are given by weight.

Based upon the evidence in this example the following vehicles lend themselves to combining PCA and CBD; propylene glycol and alcohols.

The therapeutic combination had various limitations such that the combination of delivery would not be in the same vehicles, but separately; distilled and deionized water.

Information was obtained concerning manufacturing methods. The most effective method of rapidly placing either into any vehicular solution was pre-heating the liquid to at least 100 degrees Fahrenheit and more effectively at 140 degrees Fahrenheit. However, adverse side effects were seen with some liquids. It was noted that for manufacturing or any other means of formulation that heating of CBD alone and/or in combination above 90 Fahrenheit results in a tan 'glue' or sticky material, and therefore is contraindicated. The use of CBD in alcohols at even a small percentage or other vehicles when heated to put into solution have the potential to leave a waxy or gum type of residue if used alone in disinfectants.

PCA did not leave such a residue. PCA leaves an invisible smooth non-sticky crystalline coating on the article's surface. The PCA may be seen with 1-3% concentrations. PCA is least visible following drying from a 0.25% PCA in alcohol. In water the drying in slower and on smooth vertical surfaces there is a collection of water running as dripping giving an uneven coating.

Propylene glycol may be a favored vehicle for PCA and CBD, alone or in combination. In addition, propylene glycol is FDA G.R.A.S. and therefore may be used in most every prescription route. Propylene glycol has favorable reports on skin absorption of CBD in the literature even at 1% concentration.

The reported doses for topical application therefore are between 1% and 3% depending upon the condition. 1% for skin conditions and 3% for underlying arthritic conditions.

The alcohols are preferred liquid vehicles for combinations of CBD and PCA since they allow larger concentrations but may be limited to topical route applications.

The clinical topical use concentrations of CBD and PCA together or independently should be at least 3% to leave a concentrated crystalline covering of reagent.

The examples provide information for manufacture guidelines (e.g., heating limits) as well as clinical concentrations limitations when combined. The examples also provide amounts and dosages for use in clinical medicine.

EXAMPLE

A cannabinoid/PCA liquid composition for oral delivery includes a cannabinoid/PCA composition from 0.001% to 10% by weight with at least one optional surfactant from 2-20% by weight, a solvent from 20-70% by weight, an optional preservative and/or flavoring at 0.1-5% each; and the remainder water. The cannabinoid can be cannabidiol (CBD). In another example, the composition comprises two or more surfactants, and the surfactant(s) may form a self-assembling emulsion.

The surfactants can include oleic acid, sunflower oil, lecithin, phosphatidylcholine, isopropyl myristate, stearic acid, triglycerides, polysorbate, sorbitan trioleate, sorbitan surfactants, and their combinations. The solvents can include methanol, ethanol, isopropyl alcohol, butanol, pentanol, hexanol, ethylene glycol, glycerin, propylene glycol, dipropylene glycol, glycerol, erythritol, xylitol, mannitol, sorbitol, diethylene glycol, monoethyl ether and combinations.

In embodiments, in a liquid mixture or dry tablet, pill, or solid formulation, the cannabinoid may be about 0.001%-50% by weight or preferably about 0.001%-10% by weight, or about 0.001%-3% by weight or about 0.001%-1% by weight of the total composition; and the PCA may be about 0.001%-50% by weight, preferably about 0.001%-25% by weight or about 0.001%-5% by weight, or about 0.001%-3%, or about 0.001% to about 1% by weight of the total composition.

Preferably dosage amounts would be 500 mg PCA and 20-40 mg CBD in a capsule, tablet, gummy or similar ratios in a liquid or drink mixture.

While this disclosure includes specific examples, it will be apparent after an understanding of the disclosure of this application has been attained that various changes in form and details may be made in these examples without departing from the spirit and scope of the claims and their equivalents.

The invention claimed is:

1. A pharmaceutical composition consisting essentially of a therapeutically effective amount of tetrahydrocannabinol and protocatechuic acid.

2. The composition of claim 1, wherein the tetrahydrocannabinol is about 0.001% to about 10% by weight of the total composition and the protocatechuic acid is about 0.001% to about 25% by weight of the total composition.

3. The composition of claim 1, wherein the tetrahydrocannabinol is about 0.001% to about 3% by weight of the total composition and the protocatechuic acid is about 0.001% to about 3% by weight of the total composition.

4. A method of treating cytokine mediated inflammation comprising administering a composition of claim 1, to a patient in need thereof.

5. The method of claim 4, wherein the administration comprises oral administration, inhalation, intravenous, topical, transdermal, an aerosol, pulmonary, buccal, injection, subcutaneous, and/or sublingual administration.

6. The method of claim 4, wherein the tetrahydrocannabinol is about 0.001% to about 10% by weight of the total composition and the protocatechuic acid is about 0.001% to about 25% by weight of the total composition.

7. The method of claim 4, wherein the tetrahydrocannabinol is about 0.001% to about 3% by weight of the total composition and the protocatechuic acid is about 0.001% to about 3% by weight of the total composition.

8. The method of claim 4, wherein the cytokine mediated inflammation comprises neuropathic pain, arthritis, skin inflammation and acne, chronic pain, osteoarthritis, wound healing, cartilage repair, inflammatory pain, upper respiratory inflammation, and/or joint swelling.

9. A method of treating cytokine mediated inflammation comprising administering a composition comprising protocatechuic acid and a composition comprising tetrahydrocannabinol to a patient in need thereof within about 60 minutes of each other or less.

10. The method of claim 9, wherein the administration of the composition comprising protocatechuic acid and the composition comprising tetrahydrocannabinol is done within about 15 minutes of each other or less.

* * * * *